US005386824A

United States Patent [19]

Nelepka

[11] Patent Number: 5,386,824

[45] **Date of Patent: * Feb. 7, 1995**

[54] LIGHTWEIGHT BREATHING DEVICE

[76] Inventor: Guy S. Nelepka, 2327 N. Tustin Ave., Newport Beach, Calif. 92660

[ * ] Notice: The portion of the term of this patent subsequent to Mar. 31, 2009 has been disclaimed.

[21] Appl. No.: 58,462

[22] Filed: May 6, 1993

Related U.S. Application Data

[63] Continuation-in-part of Ser. No. 528,248, May 24, 1990, Pat. No. 5,099,835, which is a continuation-in-part of Ser. No. 293,071, Jan. 3, 1989, Pat. No. 4,928,686.

[51] Int. Cl.[6] .............................................. A61M 16/00

[52] U.S. Cl. .......................... 128/204.18; 128/204.26; 128/205.24

[58] Field of Search ...................... 128/204.18, 204.26, 128/205.21, 205.22, 502.24

[56] References Cited

U.S. PATENT DOCUMENTS

| | | | |
|---|---|---|---|
| 4,798,203 | 1/1989 | Bartos | 128/205.22 |
| 4,928,686 | 5/1990 | Nelepka | 128/205.24 |
| 5,099,835 | 3/1992 | Nelepka | 128/204.18 |

*Primary Examiner*—Edgar S. Burr
*Assistant Examiner*—Aaron J. Lewis
*Attorney, Agent, or Firm*—Willie Krawitz

[57] ABSTRACT

A lightweight breathing device for underwater use, and in contaminated air is disclosed. The device employs a one-way valve which requires only one hand to effect operation, and a closure stem which is securely mounted against excessive air pressure from the valve when air is released therethrough from an attached air tank. The one-way valve includes two interfitting components, one of which is rotatable, and which provides air orifices that form an air connection upon rotation to permit the release of air from the air tank. In another embodiment, high pressure air from the air tank is passed into a piston operated pressure reducer prior to being released to the user.

11 Claims, 5 Drawing Sheets

LIGHTWEIGHT BREATHING DEVICE

This application is a continuation-in-part of U.S. Ser. No. 528,248, filed: May 24, 1990 and issued Mar. 31, 1992 as U.S. Pat. No. 5,099,835, which was a continuation-in-part of U.S. Ser. No. 293,071 filed Jan. 3, 1989, and issued May 29, 1990 as U.S. Pat. No. 4,928,686.

BACKGROUND OF THE INVENTION

This invention relates to a new and improved portable breathing device which may be employed for underwater purposes, and for use above water in contaminated air situations, and where emergency alternative air supply sources are required.

Typically, the portable breathing device of this invention is used in conjunction with a lightweight air supply for relatively short periods of time, say 2–5 minutes, or longer, depending on the capacity of the air supply tank. The device of this invention is lightweight, and of a sturdy construction, which enables it to be easily manipulated. The lightweight feature of this device permits the user a greater degree of mobility in escaping to a safe location without being encumbered by heavy air tanks or cumbersome or awkward air supply lines.

Some prior art breathing devices have employed poppet valve components which pose a hazard to the user in that they can be ejected form the device with considerable force and injure the user, or persons nearby. The present invention has the capability of providing high delivery pressures of say, 3,000–4,000 psi by means of a piston pressure reducer which enables the device to be safely used while increasing the air supply capacity of the system.

Other prior art devices use a burst disc which may pose a hazard to the user due to inadequate design.

THE INVENTION

According to the invention, there is provided a breathing device with a unique on-off air release mechanism to an air supply tank which may be operated with one hand, and a simple and safe air release closure mechanism which enable the user to release air at controlled intervals for breathing purposes.

The on-off air release mechanism includes interfitting components, one of which is rotatable, and each of these components provides air connecting orifices which permit air to be released form the air supply tank to the air release closure mechanism. Both the on-off air release mechanism and the air release closure can be operated with the same hand.

DESCRIPTION OF THE PREFERRED EMBODIMENTS

Figure 1A:
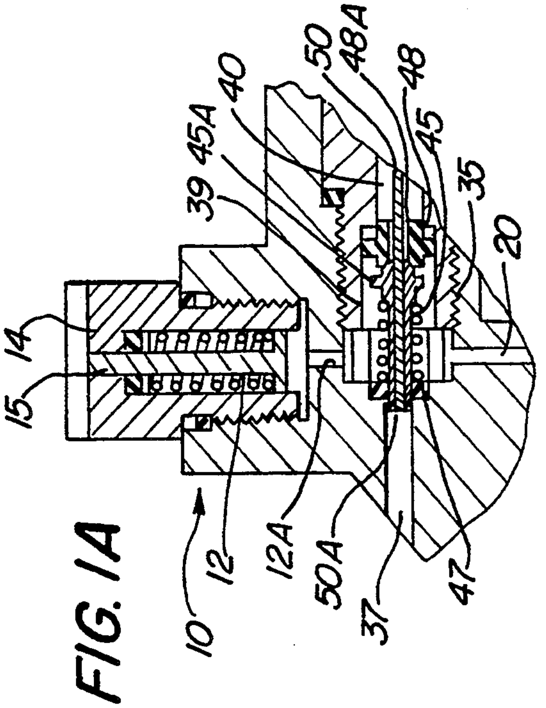
FIG. 1A is an enlarged view of a portion of FIG. 1.
Figure 1:
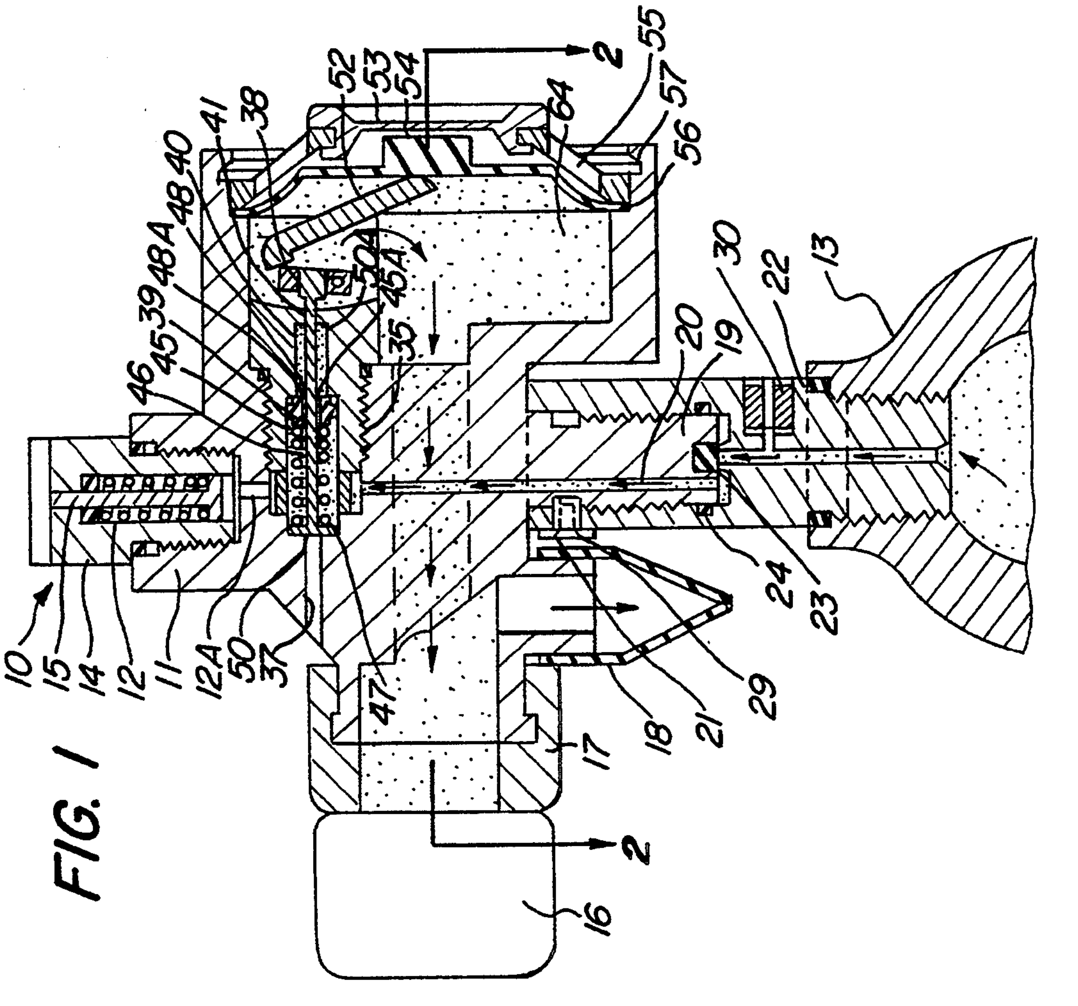
FIG. 1 is a cross sectional view in side elevation of the device of this invention.

The breathing device 10 of this invention is shown in FIG. 1, and comprises a body portion 11, fill port 12, and an air tank 13 which is filled with air through the fill port 12 and bore 12*a*, using a refill adaptor attached to a refill supply tank (not shown). When the air tank 13 has been filled, the breathing device 10 is shut off, the adaptor and supply tank are removed, and a seal plug 14 bearing a spring loaded pressure gauge stem 15 are mounted in the port 12 to seal the device. When the air tank is loaded, it weights about 2–5 pounds, with a reserve capacity of about 2–5 minutes based on continuous or intermediate breathing.

A breathing mouthpiece 16 is attached to the forward end of the device 10 through a connector 17, and an exhaust element 18 is employed to pass exhaust air from the user. An on-off housing insert valve 19 is formed as an integral part of the body portion 11 and defines an on-off center, longitudinal bore 20, and a 270 degree stop screw bore 21. The on-off housing insert valve 19, valve seat 23, and a valve O-ring 24 fit into a rotatable steel cylinder stem 25, the latter defining a burst disc port 22. A longitudinal bore 26 is defined by the cylinder stem 25 to form an air connection with bore 20 when the cylinder stem 25 rotates through a 270 degree turn. When the valve 19 turns on, it admits air from the air tank 13 into the breathing device. The rotatable cylinder stem 25 may be conveniently operated with one hand only, thereby enabling the air supply from the air tank to be easily turned on or off.

A stop screw 29 is threaded into the stop screw bore 21 to prevent turning cylinder stem 25 past the air connection region of the longitudinal bores 20 and 26. Hence, the user is not required to make any special effort or any adjustment procedures to open or close the on-off valve, since the air connection between bores 20 and 26 will occur as stop screw 29 is rotated between 70 degrees and the full 270 degrees.

A burst disc 30 is fitted into the burst disc port 22 of the cylinder stem 25 to guard against over pressurization of the breathing device, and is positioned to reduce internal or external damage to the breathing device if over pressurization occurs. Thus, if the user is holding the body portion 11 of the device, the burst disc 30 is positioned away from the user. Hence, rupture of the burst disc will occur away from the user, and will not be directed into the device.

An air regulator housing 38 is threadably mounted within a bore 35, and is air connected to the bores 20 and 26 of the housing insert valve 19 and the cylinder stem 25 through a body portion 36 positioned along lines 2—2 of FIG. 1. The body portion 36 is shown in greater detail in FIG. 2, and will be described, infra. Air pressure is balanced to ambient through an atmospheric air bore 37 which is connected to a poppet bore cavity 19 of an air regulator housing 38.

The regulator housing 38 is threadably mounted in the body portion 11, and defines the poppet bore cavity 39, a poppet stem cavity 40, and a poppet stem bore 41. A poppet 45, having a head end 45*a* is secured within the poppet bore cavity 39 of regulator housing 38 by a spring 46 and sealed at the entrance to the air pressure equalization bore 37 by an O-ring 47. The head end 45*a* of the poppet seats and seals off a regulator housing seat 48 together with an O-ring 48*a*.

A poppet stem 50 providing an integrally formed shoulder 50*a* is mounted or molded within the poppet 45 and is firmly attached thereto by means of a roughened exterior surface. Alternatively, the poppet stem 50 may employ only a roughened surface and attach within the poppet 45 without a shoulder construction. Another construction may employ the formed shoulder 50*a* mounted into a cavity bore in head end 45*a*. The poppet stem 50 passes through poppet stem cavity 40 and poppet stem bore 41, and is secured by pivot lever 51. A purge lever 52 is used to actuate the pivot lever 51 and drive the poppet stem 50 and the poppet 45 from the regulator housing seat 48, to allow air flow and purging. An adjustment screw (not shown) is adapted to preset the tension of the spring 46 so water pressure at atmospheric applied through the air equalization bore 37 will be sufficient to maintain the poppet closed.

The construction of the poppet stem 50 with a roughened surface and/or shoulder 50*a* provides a safe arrangement since it is unlikely that the poppet stem will dislodge from the poppet 45 and be driven out of the device. This will prevent injury to a user or persons nearby.

Figure 2:
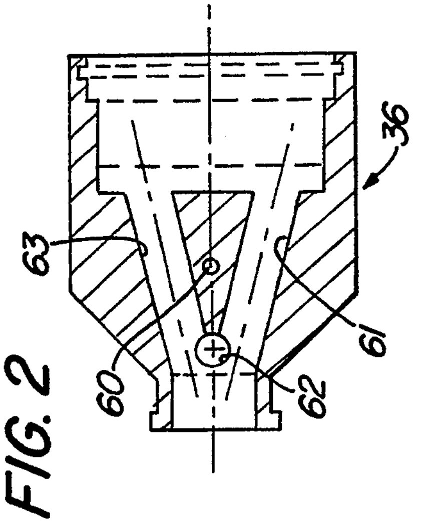
FIG. 2 is a plan view of the device, taken along lines 2—2 of FIG. 1.

Finger or suction pressure applied to the purge lever 52 will be applied to the poppet stem 50 by means of an assembly comprising a purge button 53 acting upon a diaphragm 54, the latter being reinforced by a diaphragm disc 58. The purge button 53 is surrounded by a cover 55, and the assembly is secured within a circular shoulder 56 along with a diaphragm retainer 57. When the purge button 53 is pressed, water and moisture will be expelled from the device through an exhaust bore 62 of body portion 36, and out exhaust element 18, as shown in FIGS. 1 and 2. A bore 60 of body portion 36 connects with the longitudinal bore 20 of the on-off housing insert valve 19, and admits air from the air tank 13 to the device when the cylinder stem 25 is rotated to air connect bore 26 with bore 20. When the purge button is pressed, the poppet 45 is unseated from the regulator housing seat 48. This releases or blows out water and moisture along manifolds 61 and 63 of body portion 36, through exhaust port bore 62, and to the exhaust element 18, as shown in FIGS. 1 and 2.

When the user draws on the mouthpiece 16, sufficient suction causes the poppet 45 to unseat and admit air to an inner chamber 64 along manifold channels 61 and 63 of the body 36 to the mouthpiece, and hence the user. When the user exhales, the poppet will close and exhaust air will pass through the bore 62 and out exhaust element 18.

The breathing device of FIGS. 1, 1A and 2 is adequate for pressures of about 1,800 psi. However, for higher pressures of about 3,000 psi, it would be preferred to modify the device to reduce the possibility of component blow-out, and to reduce the effects of the high pressures on the stem-poppet, cylinder springs, and gasket components. Also, it would be desirable to reduce the air pressure supplied to the user, because if the air pressure is too high, it tends to be wasted by the user.

Figure 5:
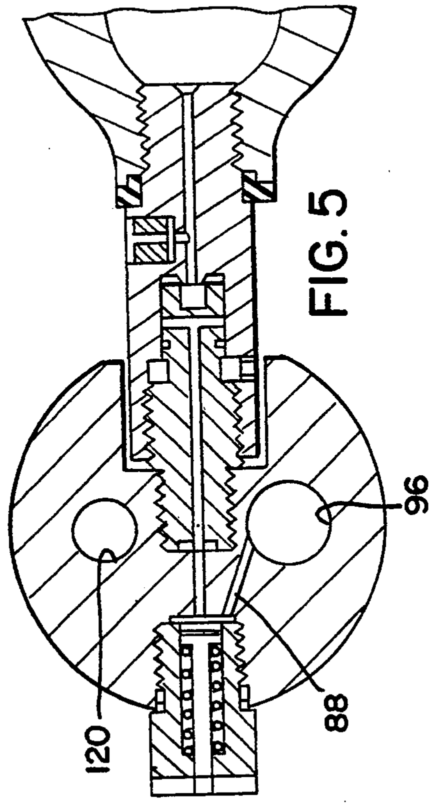
FIG. 5 is a sectional view in rear elevation showing the interconnecting air ports, and air flow from an external air supply and from an attached air supply tank of FIG. 3.
Figure 4:
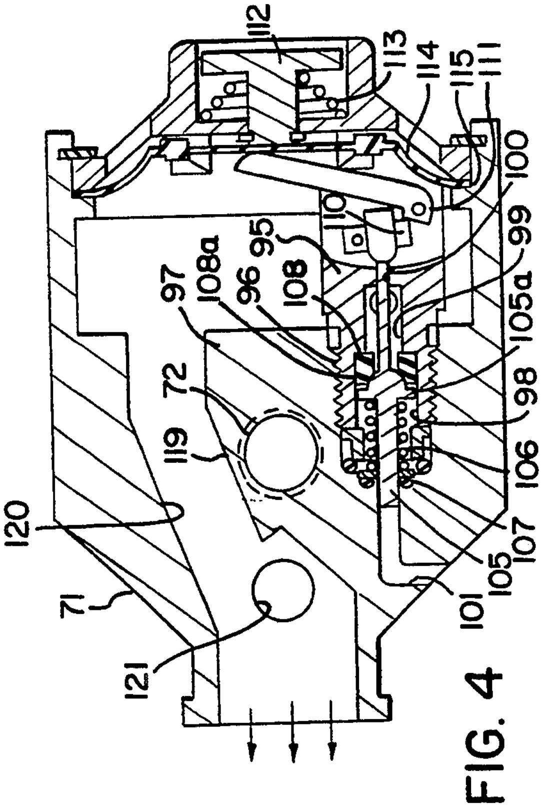
FIG. 4 is a cross sectional view in plan of the poppet valve and actuating mechanism of FIG. 3.
Figure 3:
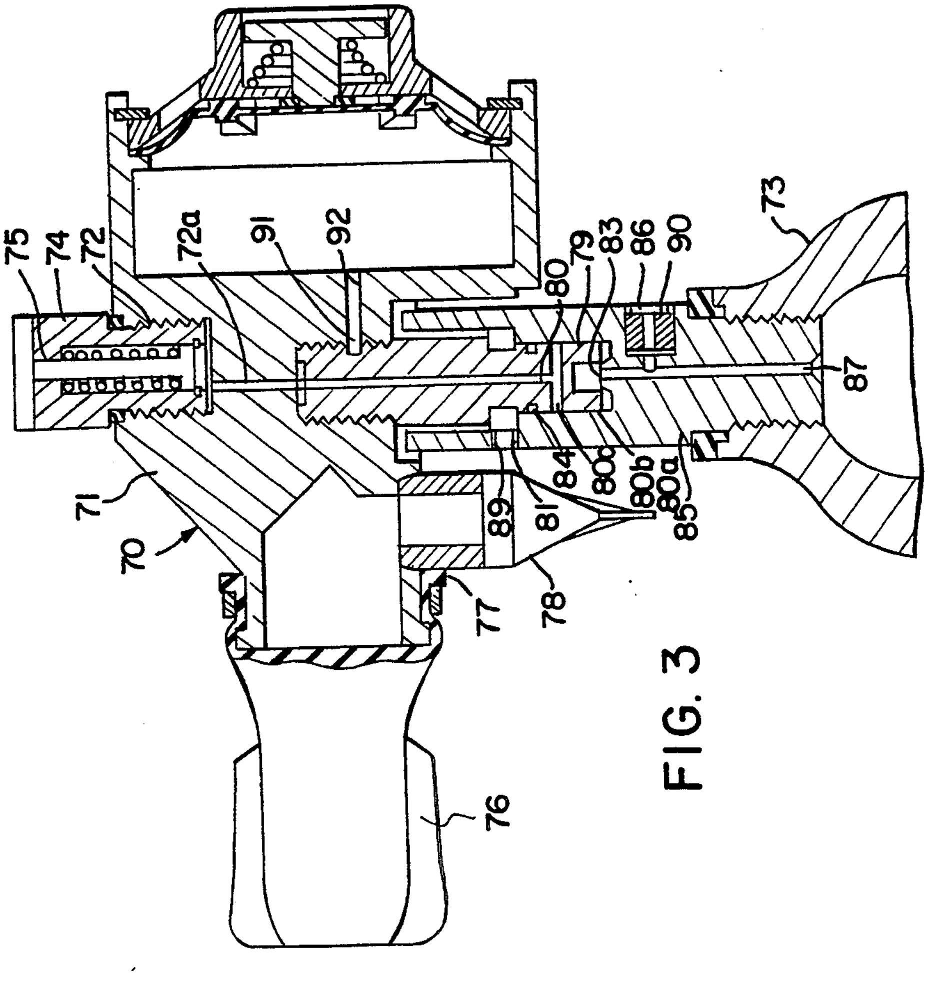
FIG. 3 is a cross sectional view in side elevation of another embodiment the device of this invention.

The modified breathing device 70 is shown in FIGS. 3, 4 and 5, and comprises a body portion 71, fill port 72, and air tank 73 which is filled with air through the fill port and bore 72*a*, using a refill adaptor attached to a refill supply tank (not shown). After the air tank 73 has been filled, the breathing device 70 is shut off and the adaptor and supply tank are removed. A seal plug 74 bearing a spring loaded pressure gauge stem 75 are then mounted in the fill port 72 to seal the device. When the tank is loaded, it weighs about 5–10 pounds, with a reserve capacity of about 7–10 minutes based on continuous or intermediate breathing.

A breathing mouthpiece 76 is attached to the forward end of the breathing device 70 through a connector 77, and an exhaust element 78 is employed to pass exhaust air from the user. An on-off housing insert valve 79 is formed as an integral part of body portion 71 and defines a longitudinal bore 80, and a 270 degree stop screw bore 81.

A chamber 80*a* is formed at the bottom of the insert valve 79 and between a cylinder stem 85. The chamber 80*a* connects with a peripheral space 80*b* which is formed between valve 79 and the stem 85. The bottom of bore 80 terminates in a space 80*c* which connects with the peripheral space 80*b*.

The on-off housing insert valve 79, a valve seat 83 and a valve O-ring 84 all fit into the rotatable steel cylinder stem 85, the latter defining a burst disc port 86. A longitudinal bore 87 is defined by the cylinder stem 85 to form an air connection with bore 80 when the cylinder stem 85 rotates through a 270 degree turn. When the housing insert valve 79 is turned on, it unseats from the valve seat 83 and air is admitted from the air tank 73 into the breathing device through connecting bore 87, chamber 80*a*, peripheral space 80*b*, space 80*c* and bores 80, 72*a*and 88, and then into a regulator housing bore 96, described, infra. The rotatable cylinder stem 85 may be conveniently operated, thereby enabling the air supply from the air tank 73 to be easily turned on or off.

When filling the air tank 73 to operating pressures, air flows linearly and directly from air port 72 and bores 72*a*, 80 and 87, while reducing air movement past the poppet-stem, spring mechanism and seals, since they are off-line from the linear flow between the air port 72 and air tank 73. Hence, wear and tear on these components is reduced despite the increase in air pressure from about 1800 psi used in the embodiments of FIGS. 1, 1A and 2, to about 3000 psi for that shown in FIGS. 3, 4 and 5.

A stop screw 89 is threaded into the stop screw bore 81 to prevent turning cylinder stem 85 past the air connection region of the longitudinal bores 80 and 87. Hence, it is not necessary for the user to make a special effort or adjustment to effect opening or closing of the on-off valve, since air connection between bores 80 and 87 will occur as the stop screw 89 is rotated between the 70–270 degree range.

A burst disc 90 is fitted into the burst disc port 86 of the cylinder 85 to guard against over pressurization of the breathing device, and is positioned to prevent any internal or external damage to the breathing device if over pressurization occurs. Thus, if the user is holding the body portion 71 of the device, the burst disc 90 is positioned away from the user. Hence, rupture of the burst disc will occur away from the user, and will not be directed into the device. A set screw 91 positioned within a bore 92 functions to prevent the insert valve from rotating due to the high pressures employed.

As shown in FIG. 4, an air regulator housing 95 is threadably mounted within a housing bore 96 in the body portion 71. The housing 95 is air connected to the bores 80 and 87 of the housing insert valve 79 and cylinder stem 85 through bores 88 and 72*a* passing through a body portion 97. Regulator housing 95 defines a poppet bore cavity 98, a poppet stem cavity 99, and poppet stem bore 100. Air pressure is balanced to ambient through an air equalization bore 101 which is connected to the poppet bore cavity 98 of the air regulator housing 95.

A poppet 105, having a head end 105*a*, is secured and biased by a spring 106 within the poppet bore cavity 98 of the air regulator housing 95. The poppet is sealed at the entrance to the air pressure equalization bore 101 using an O-ring 107. Head end 105*a* of the poppet seats and seals off a regulator housing seat 108 in conjunction with an O-ring 108*a*. A poppet stem 109 is shown integrally formed with the poppet 105. Alternatively, the poppet stem can be secured or molded into the poppet in a similar manner as shown in the embodiments of FIGS. 1, 1A, and 2.

Poppet stem 109 passes through poppet stem cavity 99 and poppet stem bore 100, and is driven by pivot lever 110. A purge lever 111 actuates a pivot lever 110, which is driven by a purge button 112 biased by a spring 113 which is secured by a diaphragm 114 mounted on a circumferential shoulder 115.

As shown in FIG. 4, a manifold area 119 is mounted within the body portion 91 and defines a single channel 120 which connects from the air regulator housing to the breathing mouthpiece 76, as shown by the arrows; exhaust air is fed through bore 121. Use of the single channel 120, rather than the double channel 61 and 63 as shown in FIG. 2, enables better control of the air intake by the user. This control by the user is particularly important when the device is employed at a relatively higher pressure of 3000 psi, and reduces the tendency of a user to waste air. Operation of the purge button 112 and the device 70 is the same as described for the embodiments of FIGS. 1, 1A and 2.

The device of this invention is simple to operate, and the components of the breathing device do not present a problem of exploding parts. Use of the present device, when underwater, can become critically important as a back-up device if a major air system fails, because it is portable and totally independent of the major air supply system, and it enables the user adequate time and leeway to escape due to failure of a life support system. It will also be appreciated that in a smoke or contaminated air environment, the lightweight nature and ease of operation enables a user to avoid reliance on a much heavier air supply system. The same situation would prevail if there were no available air supply system or if a permanently attached air supply system were to malfunction or fail.

FIGS. 6–9 show another embodiment of this invention designed to improve the safety of the device, using air tank pressures at high pressures of, say 3,000–4,000 psi. Improved safety in this case involves reducing the possibility of component parts being ejected from the device, and for the intake of air at excessive pressures in the event of component failure.

Figure 6:
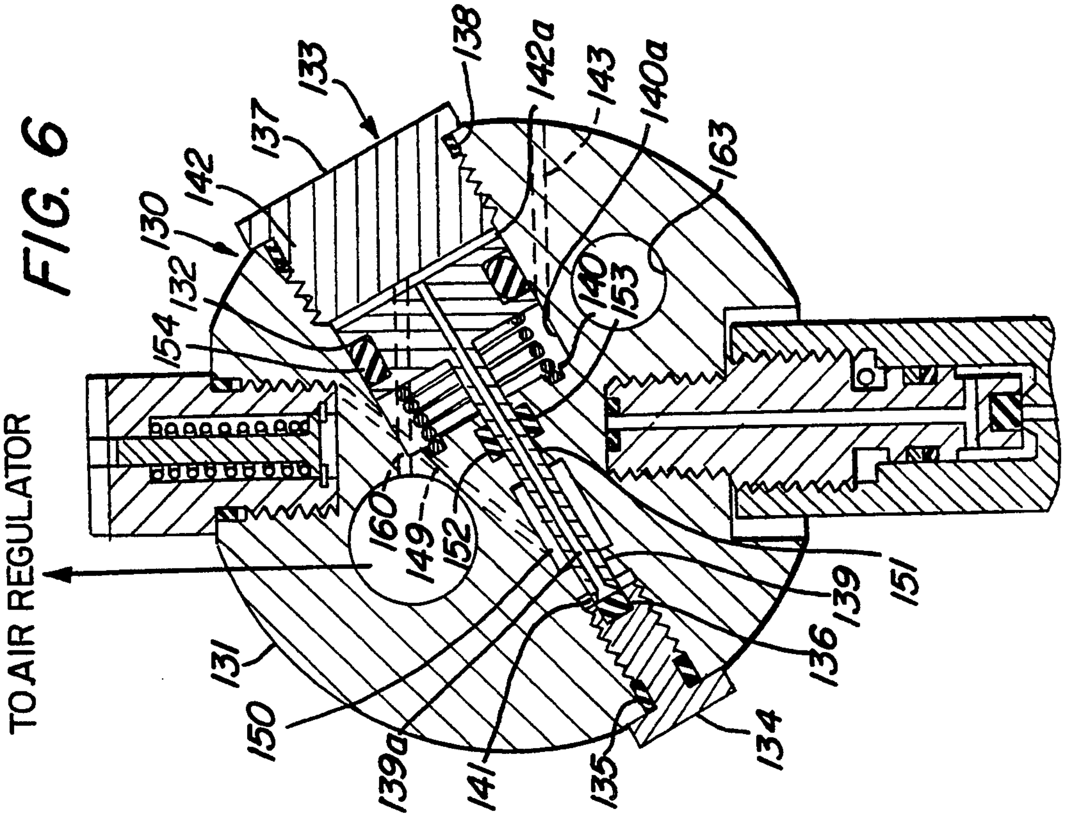
FIG. 6 is a sectional view of another embodiment of this invention, in rear elevation, showing the interconnecting air ports, and air flow from an external air supply, and from an attached air supply tank through a piston pressure reducer.
Figure 9:
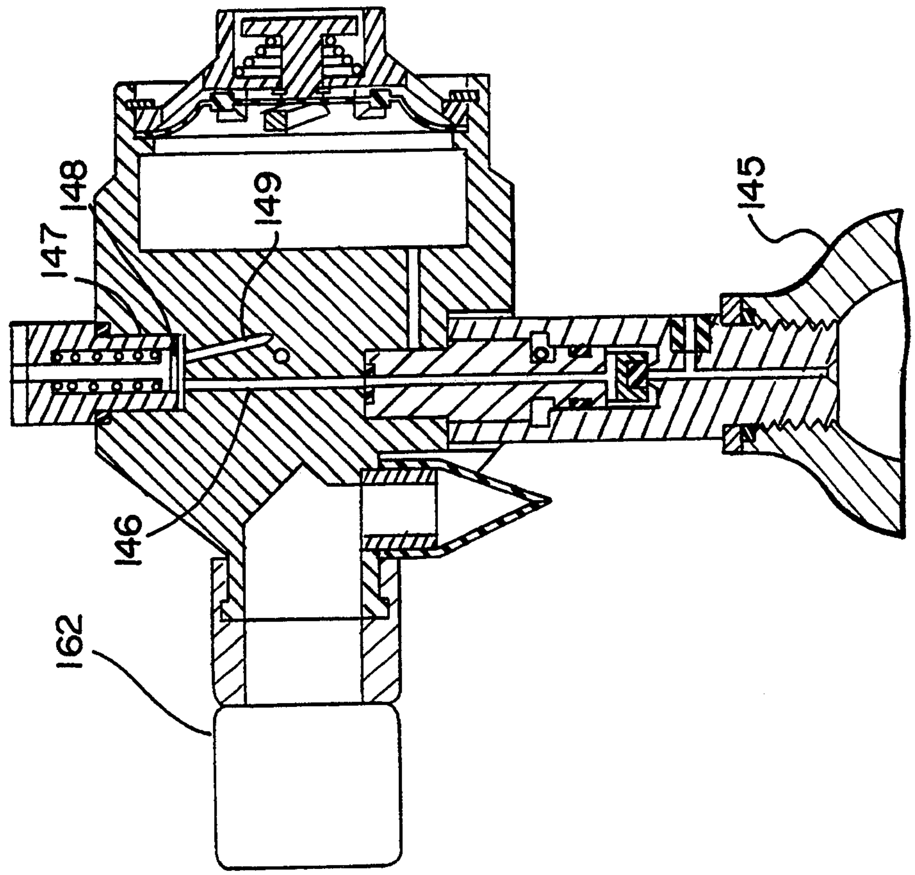
FIG. 9 is a cross sectional view of FIG. 6, and similar to FIG. 3, showing the internal air bore connection from the attached air supply tank to the piston pressure reducer; and, FIG. 10 is a cross sectional view of the device showing another embodiment similar to FIG. 6.

FIGS. 6 and 9 show a breathing device 130 similar to FIGS. 1–4, having a body 131 defining an internal bore 132 into which is mounted a piston pressure reducer 133. As shown in FIG. 6, the pressure reducer is mounted within the body 131 of the breathing device, and comprises a solid high pressure plug 134 mounted at one end within the bore 132, and sealed against air leakage with a sealing ring 135. A valve seat 136 is mounted centrally at the end of the plug 134. The other end of the piston pressure reducer 133 comprises a solid plug 137 mounted within the bore 132 which is also sealed against air leakage with a sealing ring 138.

A hollow piston element 139 defining a bore 139*a* is mounted within the internal bore 132 and between the plugs 134 and 137, and is biased towards the high pressure plug 134 by a spring 140 secured within a spring chamber 140*a*. A nigh pressure air equalization bore 143 leads from the spring chamber 140*a* of the piston element to ambient. The nigh pressure end 141 of the piston element 139 forms a closure on the valve seat 136 at the end of plug 134 due to the applied biasing pressure of spring 140. The low pressure head 142 of the piston element 139 is spaced from the plug 137 and forms an air gap 142*a*therebetween, and the bore 139*a* of the piston element 139 forms an air communication with the gap 142*a*.

As shown in FIG. 9, air from a supply tank 145 is passed along a central bore 146 to the inlet bore 147 of the air breathing device 130, along space 148 of the inlet bore 147, and to an air passage bore 149 which connects to the piston element 139 through a piston alignment bushing 150.

Sealing against air leakage along the interface 151 between the piston element 139 and the internal bore 132 is provided by seals 152, 153 and 154. High pressure air from the air supply tank 145 which is passed into the bushing from the air passage bore 149 is diverted by the seals 152, 153 and along the interface 151 down to the high pressure end 141 of the piston element 139. When sufficient airflow pressure is applied from the air supply tank 145, it will produce an opposing air pressure of about 3,000 psi–4,000 psi against spring 140 and almost counterbalance the biasing force of the spring 140 on the piston, without causing the piston end 141 to unseat from the valve seat 136.

Figure 7:
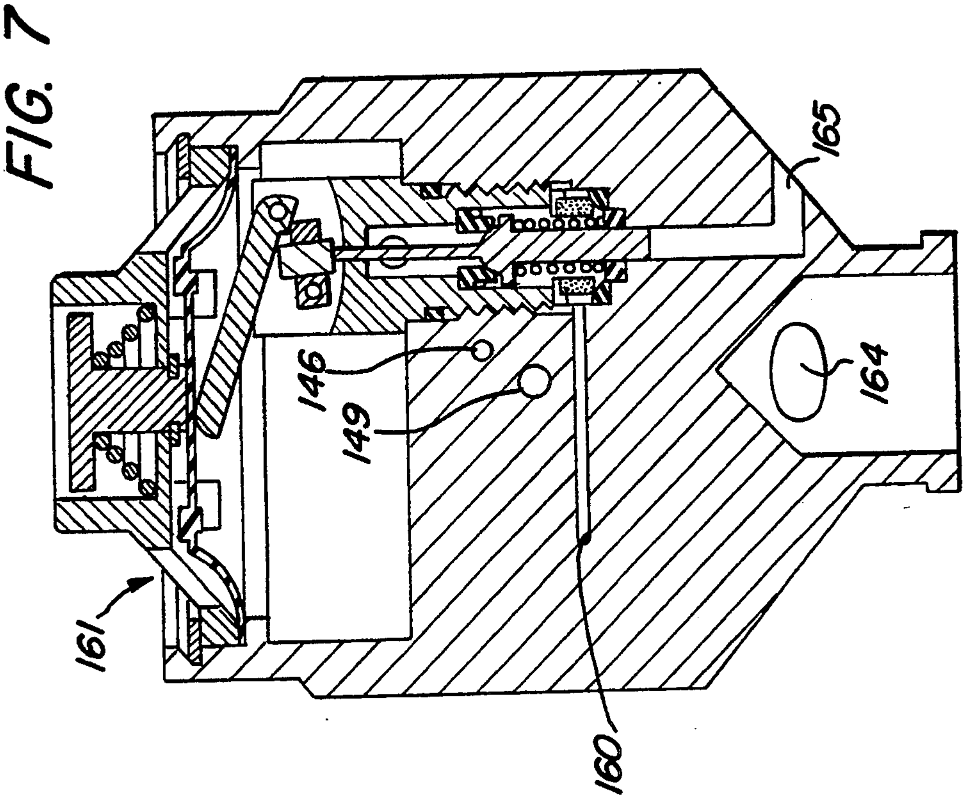
FIG. 7 is a cross sectional view in plan of the popper valve and its actuating mechanism, when used in conjunction with the device shown in FIG. 6.

As shown in FIGS. 6 and 7, a bore 160 leads from the air gap 142*a*of the piston 139 to the intake of an air regular 161 which operates in the same manner as shown in FIGS. 3 and 4. Since the operation of regulator 161 is the same, the details of the regulator are not further described.

Figure 8:
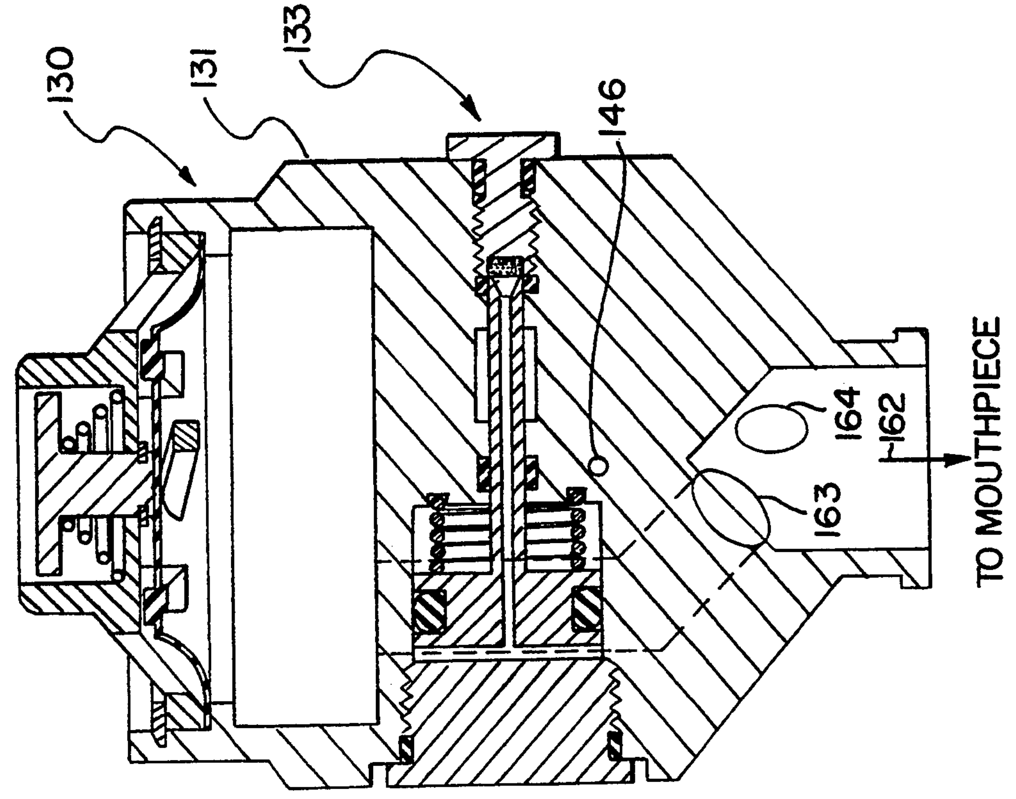
FIG. 8 is a cross sectional view of FIG. 6, illustrating the air connection from the piston pressure reducer to the mouthpiece of the device and to exhaust.

FIGS. 7 and 8 illustrate the connection from the air regulator 161 via an air bore 163 to the mouthpiece 162, and an exhaust port 164. An air equalization bore 165 leading from the air regulator 161 to ambient, performs the same function as the air equalization bore 143.

In operation, when air pressure is applied from the supply tank 145, it will act upon piston pressure reducer 133 to oppose the biasing action of the spring 140. When the end of the piston 139*a* is unseated from the valve seat 136, it is sized to be displaced about 2–3 mils. This displacement combined with an internal diameter size of bore 139*a* of about 0.75", and with an initial air pressure from supply tank 145 of about 3,000 psi–about 4,000 psi, the biasing of spring 140 and air regulator 161 can be downwardly adjusted. Thus, air pressure to the user is reduced to about 75 psi–140 psi. Care, of course, is required when operating this device.

Figure 10:
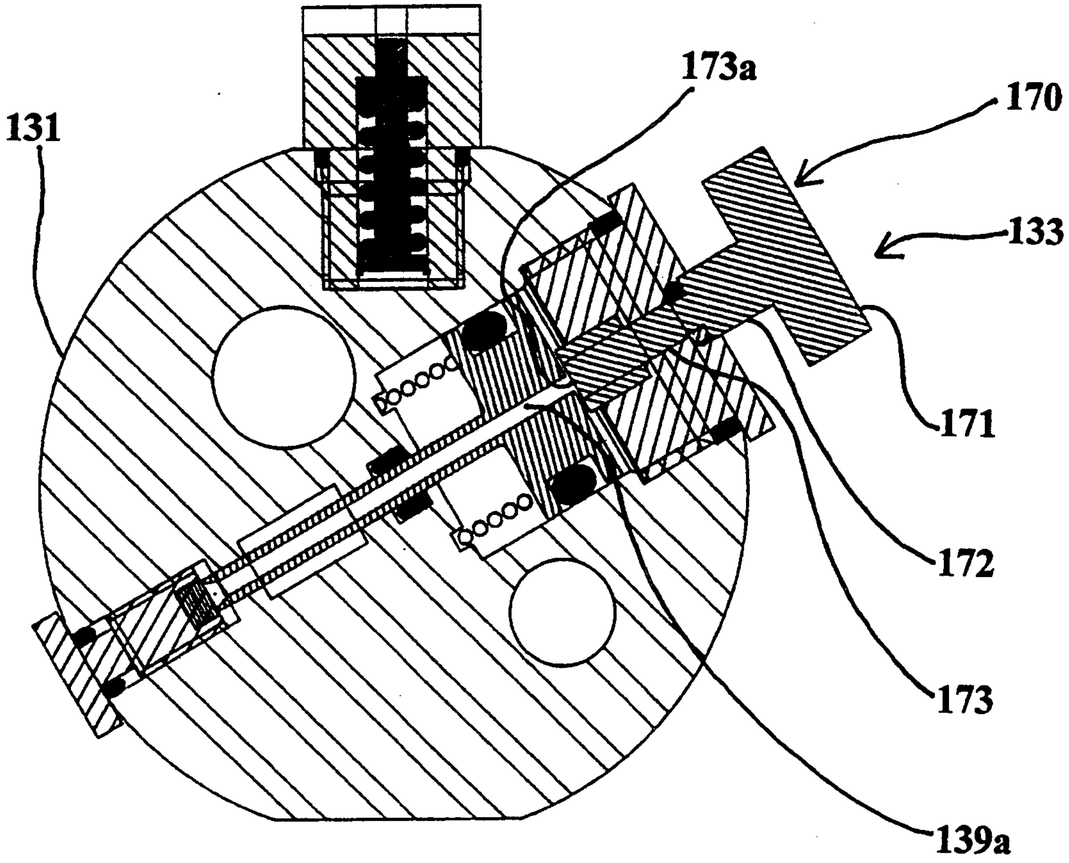

FIG. 10 shows another embodiment similar to FIG. 6 in which air flow through the piston pressure reducer 133 is controlled by movement of a threadably mounted control element 170, which defines a handle portion 171, and stem portions 172 and 173. The end 173*a* of the stem portion 173 seats over the bore 139*a* of the pressure reducer 133, so that when turned inwardly, the stem portion 173 will seal off bore 139*a*. This will prevent air from reaching the device from air tank 145.

As shown in FIG. 10, pressure reducer 133 is connected directly to the air tank 145 by the air bore 149 (as shown in FIG. 7.). This enables reducer 133 and control element 170 to replace the on-off insert valves 19 or 79 for purposes of controlling air flow from the air tank 145. If desired, the pressure reducer 133 can be oriented to align it with the air tank in a similar fashion as the insert valves 19 or 79.

I claim:

1. An air breathing device comprising:

a.) a main body including a fill port for supplying air to an air supply tank mounted on the breathing device;

b.) a rotatable cylinder stem defining a first orifice bore, the cylinder stem being mounted on the breathing device and attached to the air supply tank, the first orifice bore being connected to the air supply tank;

c.) an on-off valve mounted on the cylinder stem and defining a second orifice bore, the first and second orifice bores forming an air communication upon sufficient rotation of the cylinder stem, thereby turning on and admitting air from the air supply tank to the device;

d.) an air regulator housing mounted within the main body and connecting from the second orifice bore to a popper bore cavity;

e.) piston means mounted within the main body and connected to the regulator housing and the air supply tank, the piston means reducing air pressure from the air supply tank and the air regulator;

f.) an elongate, spring loaded poppet means defining a longitudinal, axial bore, one end of the poppet means seating into an atmospheric bore, and an opposed end of the poppet means, including a poppet head, seating into and sealing the poppet bore cavity, and a poppet stem mounted and secured within the longitudinal, axial bore;

g.) a body portion mounted in the on-off valve and providing an air connection between the valve and the popper means of the air regulator housing;

h.) a breathing mouthpiece and exhaust port mounted on the air breathing device, the breathing mouthpiece being air connected through the body portion to the air regulator, housing and the poppet bore cavity, the exhaust port being connected to the body portion; and, i.) a lever adapted to actuate the stem of the popper means, the poppet stem being connected to the lever through a popper stem cavity contiguous with the popper bore cavity and secured in the popper seem cavity by a shoulder on the poppet stem; whereby:

i. when the on-off valve is turned on, and a user inhales on the mouthpiece, sufficient suction is produced to unseat the popper valve from the popper bore cavity and admit air to the user from the air supply tank and through the connected first orifice bore, and then through the body portion;

ii. when the user exhales on the mouthpiece, the popper closes and exhaust air passes through the body portion to the exhaust port; and, iii. when the lever is pressed, the poppet will be unseated ad release or blow out water and moisture through the body portion and exhaust port.

2. The air breathing device of claim 1, in which air pressure from the air supply tank is reduced from about 3,000 psi–4,000 psi to about 75–140 psi.

3. The air breathing device of claim 1, including an air cylinder attached to the cylinder stem for supplying air therethrough.

4. The air breathing device of claim 1, in which the poppet stem provides a roughened surface to firmly attach the poppet stem to the poppet.

5. The air breathing device of claim 1, in which the breathing mouthpiece is air connected to the air regulator housing by a single manifold.

6. The air breathing device of claim 1, in which the poppet stem, at an end remote from the poppet head, is positioned for movement within an atmospheric air bore, and water or air at atmospheric pressure will maintain the poppet closed.

7. The air breathing device of claim 1, in which the piston means is connected directly to the air tank by an air bore, and a control element is provided to seal the connection between the air tank and the piston.

8. The air breathing device of claim 7 in which the control element is mounted on the piston means.

9. The air breathing device of claim 8, in which the piston means defines an air passageway therethrough which is connected to the said air bore, and the control element is rotatably mounted on the piston means and adapted to seal and unseal the said air passageway during rotation.

10. An air breathing device, comprising:

a.) a main body portion, including a fill port for supplying air to an air supply tank mounted on the breathing device;

b.) an air regulator housing mounted within the main body portion and connecting to a poppet bore cavity;

c.) piston means mounted within the main body for connecting the air regulator housing directly with the air supply tank, the piston means reducing air pressure from the air supply tank to the air regulator;

d.) a control element mounted on the piston means and adapted to seal and unseal the connection between the piston means and the air supply tank;

e.) an elongate, spring loaded poppet means connected to the air regulator housing, the poppet means defining a longitudinal, axial bore, one end of the poppet means seating into an atmospheric bore, and an opposed end of the poppet means, including a poppet head, seating into and sealing the poppet bore cavity, and a poppet stem mounted and secured within the longitudinal, axial bore of the poppet;

f.) a breathing mouthpiece and exhaust port mounted on the air breathing device, the breathing mouthpiece being air connected through the main body portion to the air regulator, housing and the poppet bore cavity, the exhaust port being connected to the main body portion; and, g.) a lever adapted to actuate the stem of the poppet means, the poppet stem being connected to the lever through a poppet stem cavity contiguous with the poppet bore cavity and secured in the poppet stem cavity by a shoulder on the poppet stem; whereby:

i. when the control element is turned on, and a user inhales on the mouthpiece, sufficient suction is produced to unseat the poppet valve from the poppet bore cavity and admit air to the user from the air supply tank, through the connected piston means and then through the main body portion;

ii. when the user exhales on the mouthpiece, the popper closes and exhaust air passes through the main body portion to the exhaust port; and, iii. when the lever is pressed, the poppet will be unseated and release or blow out water and moisture through the main body portion and exhaust port.

11. The air breathing device of claim 10, in which the said piston means defines a central bore connected to the air supply tank, and the control element is rotatably mounted on the said piston means and adapted to seal and unseal the central bore.

* * * * *